United States Patent [19]

Mora

[11] Patent Number: 4,652,568
[45] Date of Patent: Mar. 24, 1987

[54] THEOPHYLLINE-7-ACETIC ACID ESTER OF D,L-TRANS-SOBREROL HAVING MUCOSECRETOLYTIC-FLUIDIZING AND ANTIBRONCHOSPASTIC ACTIVITY, A PROCESS FOR ITS PREPARATION AND PHARMACEUTICAL COMPOSITIONS THEREOF

[75] Inventor: Camillo C. Mora, Piacenza, Italy
[73] Assignee: Camillo Corvi S.p.A., Italy
[21] Appl. No.: 711,665
[22] Filed: Mar. 14, 1985
[30] Foreign Application Priority Data
Apr. 2, 1984 [IT] Italy ................................ 20353 A/84
[51] Int. Cl.⁴ .................... C07D 473/08; A61K 31/52
[52] U.S. Cl. .................... 514/263; 544/267; 544/273
[58] Field of Search ...................... 544/276, 277, 267; 514/263

[56] References Cited

U.S. PATENT DOCUMENTS 2,756,229 7/1956 Stoll et al. ........................ 544/267
3,632,742 1/1972 Eckat et al. ...................... 544/267
4,120,947 10/1978 Diamond ............................ 514/263

Primary Examiner—Nicholas S. Rizzo
Attorney, Agent, or Firm—Ostrolenk, Faber, Gerb & Soffen

[57] ABSTRACT

A novel theophylline-7- acetic acid ester is described. Said ester is obtained by reacting, at a temperature from 1° to 20° C., theophylline-7-acetic acid chloride with d,l-trans-sobrerol.

There are further described pharmaceutical compositions with mucosecretolytic-fluidizing and antibronchospastic activity containing the novel ester.

7 Claims, No Drawings

THEOPHYLLINE-7-ACETIC ACID ESTER OF D,L-TRANS-SOBREROL HAVING MUCOSECRETOLYTIC-FLUIDIZING AND ANTIBRONCHOSPASTIC ACTIVITY, A PROCESS FOR ITS PREPARATION AND PHARMACEUTICAL COMPOSITIONS THEREOF

DESCRIPTION

The object of this invention is a theophyllineacetic acid ester of d,l-trans-sobrerol, having the following formula:

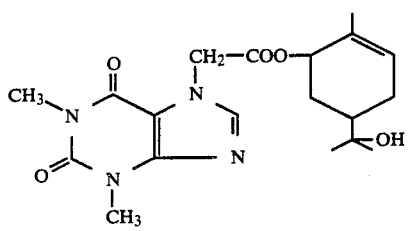

Code CO/1488) mol. wt. 390.40

5-hydroxy-α,α-4-trimethyl-3-cyclohexene-1-methanol-5-[2[7[1,2,3,6-tetrahydro-1,3-dimethyl-2,6-tetrahydro-1,3-dimethyl-2,6-dioxopurinyl]]]-acetate.

d,l-trans-sobrerol is known due its employment in therapy for respiratory diseases, since it acts as a mucoregulator and expectorant.

It has now been found that the ester of formula (I), besides maintaining, with a slight potency increase, the mucosecretolytic and fluidizing activity of d,l-trans-sobrerol, combines in the derivative of formula (I) the antibronchospastic properties characteristic of the xanthine derivatives as it is, in the present case, the theophylline-7-acetic acid.

In the novel bifunctional molecule as obtained according to the present invention, there are in accord well-balanced quantitative dosages between the mucose-cretolytic component of the d,l-trans-sobrerol moiety and the antibronchospastic one originated from the xanthine moiety of theophylline-7-acetic acid, thereby providing for a perfectly compatible complex for the cases of respiratory apparatus diseases, characterized in a bronchial hypersecretion accompanied by dysponoea or asthma forms.

An object of this invention is further to provide a process for the preparation of the novel bifunctional molecule, consisting of condensating the theophylline-7-acetic acid chloride of formula (II) with d,l-trans-sobrerol.

The condensation occurs in an aprotic environment of solvents such as tetrahydrofuran, dioxane, anhydrous methylene chloride free from ethanol, in the presence of an organic base, such as triethylamine at a very slight excess as to the stoichiometric amount. The reaction is completed by the usual neutralization, washing and concentration procedures, up to the pure product (I) precipitation. The process according to this invention is illustrated, thie being, however, not limiting for the same, by Example 1.

EXAMPLE 1

5-hydroxy-α,α-4-trimethyl-3-cyclohexene-1-methanol-5-[2[7[1,2,3,6-tetrahydro-1,3-dimethyl-2,6-dioxopurinyl]]]acetate

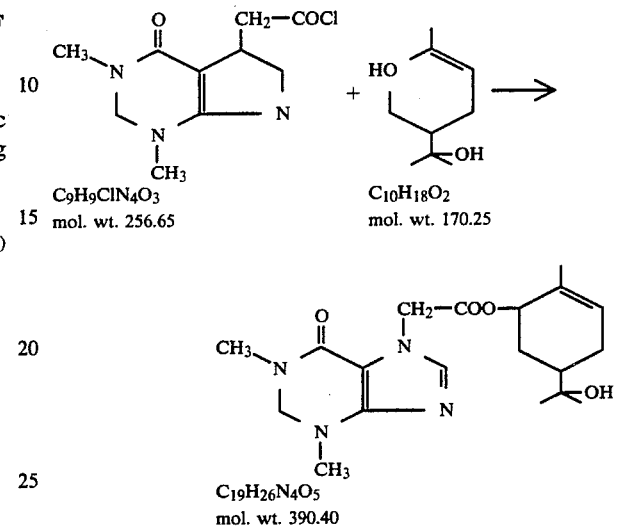

To a solution of 34 g. (0.2 mole) of d,l-trans-sobrerol in 200 ml of tetrahydrofuran containing 30 ml (0.21 mole) of triethylamine there are added, slowly, under stirring and cooling at 1° C., 52 g (0.203 mole) of theophylline-7-acetic acid chloride, dissolved into 400 ml of tetrahydrofuran. The reaction mixture is kept under stirring overnight (about 12 hours) and it is then poured into 1.5 liters of 5% diluted $H_2SO_4$. The mixture is extracted with ethyl acetate (3×500 ml). The combined organic phases, after separation, are washed with an aqueous 5% sodium bicarbonate solution, and then with water.

The reaction mixture is anhydrified with anhydrous $MgSO_4$ and is concentrated to a volume of about 400 ml; it is cooled externally with ice-water and the precipitate is filtered, to give 46 g of a white crystalline product with a m.p=162°-168° C. Theoretical yield=59%.

ANALYTICAL CHARACTERIZATION OF THE COMPOUND OF FORMULA (I)

Elemental analysis for $C_{19}H_{26}N_4O_5$ mol. wt. 390.443: Calculated %: C=58.45; H=6.71; N=14.35; O=20.49. Found %: C=58.51; H=6.59; N=14.38 (Average of 3 determinations).

I.R. Spectrum (nujol dispersion; $cm^{-1}$) 3460 and 3410=γ OH, 1750 γ C=O ester, 1705, 1655, 1558 γ CO γ CN of the xanthine moiety, 1210, 920 and 750 characteristic bands.

$H^1$ N.M.R. spectrum ($CDCl_3$ solvent T.M.S. references; δ p.p.m.) 7.55 s. (IH; N=CH), 5.75 centre, c.a. (1H; C=CH), 5.28 centre, c.a. ($^1\overline{H}$; $W\frac{1}{2}$=8 Hz; COO-CH—C), 5.04 and 4.93 AB system (2H, $J_{AB}$=16 Hz; N—CH_2—CO, 3.57 s. (3H; CO—N(CH_3)CO), 2.4–1,3 c.a. (5H; C—CH_2—CH—CH_2C=, 1.7 b.s. (3H; CH_3—C=C), 1.22 and 1̄1̄0 s. (3H each; gem. CH_3).

Legend: S=singlet; $W_\frac{1}{2}$=broadness at half height; b.s.=broadened singulet T.M.S.=tetramethylsilane; c.a.=complex absorption.

Mass spectrum (quadrupole direct insertion, 80 eV; 70 mA; m/z): 390 (M+; 0,2%) 375 [(M-15)+; 0,1%]; 372

[(M-18)+; 0,1%]; 332 (0,15%); 239 (55); 194 (20); 193 (15); 152 (5); 137 (16); 135 (13); 109 (17); 94 (59), 93 (75); 79 (80); 59 (base peak).

ACUTE TOXICITY

Method for studying $LD_{50}$ in the mouse after a single oral administration.

Groups of 10 Swiss albine, female, adult mice (20–22 g), fasting from the evening preceding the test, are treated orally with various doses (4 to 5) of the test drugs, dissolved/suspended in 1% hydroxycellulose (volume administered 20 ml/kg). Thereafter, the animals are fed again (Morini MIL fodder for mice).

The 50% lethal dose ($LD_{50}$) is calculated by the method of Litchfield J. T. and Wilcoxon F. (J. Pharmacol. 96, 99–113, 1949) by utilizing the mortality data as obtained at the 14th day after the drug treatment.

| Substance | $LD_{50}$ in mg/kg |
|---|---|
| CO/1488 | 1900 |
| d,l-trans-sobrerol | 2340 |
| theophylline | 284 |

ANTIBRONCHOSPASTIC ACTIVITY

Method of Konzett and Rössler (Arch. exp. Pathol. Pharmakol. 195, 71–74, 1940).

Spotted female guinea-pigs, with a body weight of 300–500 g., are used. The animals are an aesthetized by an intraperitoneal urethane injection (1.25 g/kg) and, in order to block the spontaneous breathing, tubocurarine (~10 mg/kg) intravenously (i.v.) is administered. The trachea of the animal is connected by means of a cannula to a Starling type pump (mod. 681) of Harward Apparatus, and to a Basile transducer (Comerio—VA, mod. 7020); the latter is connected to a Basile Unirecord mod. 7050 microdynamometer for graphic recording of the bronchospasm.

As a spasmogenous agent, hystamine (6 to 20 mg/kg i.v.) is used. The activity is defined as percent inhibition of the bronchospasm induced by hystamine in the presence of the drug (i.v. administered), compared to the one of hystamine alone in the presence of the solvent.

The drugs are dissolved into 2% dimethylformamide in physiological solution (solvent).

TABLE No. 2

Antibronchospastic activity in the guinea-pig. Drug administration by intravenous way.

| Subtance | Activity |
|---|---|
| CO/1488* | 143 |
| theophylline | 100 |
| d,l-trans-sobrerol | 0 |

*The activity of the compound of formula (I) of this invention is based on the theophylline, taken equal to 100.

BRONCHOSECRETAGOGUE ACTIVITY

Method of mucoproduction in the rabbit according to Scuri R. et al, Boll. Chim. Farm. 119, 181-7, 1980.

Male brown rabbits weighing 2.8–3.5 kg are used. To said animals, by a surgical operation under anaesthesia, a T shaped tracheal cannula is applied, as described in the above mentioned bibliographic reference.

To the cannula, a container (a polypropylene 2 ml test tube) is applied for periodical collection of the bronchial secretion.

The study of mucoproduction, started at the fourth day after the operation, is divided into two 4 hour periods for collecting and measuring the mucus, and precisely from 8:30 to 12:30 (I) and from 12:30 to 16:30 (II).

The activity of each drug is tested by administering the same by oesophageal way (os) at the begining of the II period and by evaluating the percent increase of mucoproduction (weight of the mucus as collected) over the II period as compared to the I period.

TABLE No. 3

Bronchosecretagogue activity in the rabbit. Oral drug administration.

| Substance | Activity |
|---|---|
| CO/1488* | 128 |
| d,l-trans-sobrerol | 100 |
| theophylline | 0 |

*The activity of the compound of formula (I) of this invention is based on the d,l-trans-sobrerol, taken equal to 100.

FLUIDIZING "IN VIVO" ACTIVITY

Method for studying viscosity of the bronchial mucus of a bronchitic rabbit. (R. Scuri et al.—Il Farmaco, Ed. Pr., 36, 36–48, 1981).

Male rabbits weighing 2.7–3.5 kg, made bronchitic by sulphuric acid aerosol treatment according to the method of Cantarelli (G. Cantarelli et al—Il Farmaco, Ed. Pr. 34, 393–416, 1979) are treated with the test drugs and the bronchial mucus is collected by means of a tracheal cannula according to the procedure of R. Scuri (R. Scuri et al.—Boll. Chim. Farm. 119, 181-7, 1980). Viscosity of the mucus as withdrawn is studied by using a Contraves RM16 microviscosimeter and it is recorded by a Rheomat 15T-FC apparatus.

TABLE No. 4

Fluidizing "in vivo" activity of bronchial mucus of bronchitic rabbits. Oral drug administration.

| Subtance | Activity |
|---|---|
| CO/1488* | 110 |
| d,l-trans-sobrerol | 100 |
| theophylline | 0 |

*The activity of the compound of formula (I) of this invention is based on the d,l-trans-sobrerol taken equal to 100.

PHARMACOCINETICS

Two groups of Wistar rats (165÷250 g) are utilized. Before treatment, the animals were fasting for about 15 hours and were allowed to drink a 10% glucose solution ad libitum.

To the first group, the compound of formula (I) of this invention, orally (transoesophageal intubation) at the dose of 300 mg/kg is administered (a single administration) and at 0.5 h; 1 h; 1.5 h; 2 h; 3 h; 4 h; and 6 h from administration 5 rats/time are sacrificed. The blood, as collected into test tubes containing sodium heparin is centrifuged, and the plasma so obtained is utilized for quantitative analysis of the product, by means of high pressure liquid chromatography (HPLC) with an U.V. detector. To the second group, the compound of formula (I) of this invention at the dose of 300 mg/kg orally is administered (a single administration), and at 1 h and 2 h from administration, 5 rats/time are sacrificed (by bleeding). To each rat, trachea, bronchia and lungs are withdrawn. From trachea and bronchia, by means of two washings with a 0.5 ml syringe containing physiological solution, introduced into the trachea, the tracheo-bronchial excretion is recovered, which is utilized to evaluate quantitatively the presence of the compound of formula (I) of the present invention. The pulmonary tissue, to which a KCl solution has been added, is homogenized by an ultra Turrax apparatus and utilized for the quantitative testing of the presence of the compound of formula (I) of this invention. The course of the plasmatic levels showed indicative of a quick and good absorption of the drug. Further, the compound of the invention is found also at the level of tracheo-bronchial mucus as well as in the pulmonary parenchyma. In relation to the activity shown on by the compound of the invention as a mucosecretolytic-fluidizing-antibronchospastic agent, the present invention further provides pharmaceutical compositions containing the compound of formula (I) of this invention in dosage units.

The therapeutical dose which may be expected for man is of 800/600 mg pro die.

The pharmaceutical forms containing said active component, are preferably those of oral and rectal administration and in particular: capsules, tablets, syrup, granules in little bags, and suppositories.

As excipients one may employ, for the oral pharmaceutic forms: starch, lactose, microgranular cellulose, polyvinylpyrrolidone, sorbitol and, more generally, diluent, bonding, lubricating, aromatizing, flavour masking and sweetening agents.

For the suppository form, as excipients triglycerides of saturated fatty acids, lecithius and phospholipids of more common pharmaceutical use are employed.

I claim:

1. 5-hydroxy-α,α4-trimethyl-3-cyclohexene-1-methanol-5-[2[7[1,2,3,6-tetrahydro-1,3-dimethyl-2,6-dioxopurinyl]]]acetate, of formula:

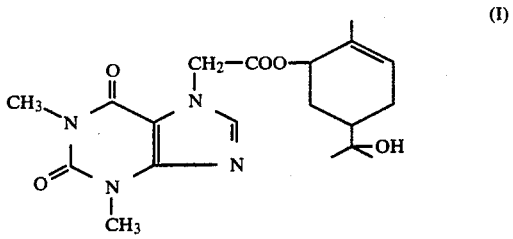

2. A process for preparing the compound of formula (I) of claim 1, characterized in that d,l-trans-sobrerol and theophylline-7-acetic acid chloride are condensed in a aprotic organic solvent in the presence of a slight excess of an acid acceptor organic base and under cooling.

3. The process according to claim 2, characterized in that the condensation reaction is carried out in tetrahydrofuran at a temperature from 1° to 20° C. in the presence of triethylamine at the molar ratio, based on the acid chloride as employed, of 1.03–1.05:1

4. The process according to claim 2, characterized in that dioxane is used as the solvent.

5. The process according to claim 2, characterized in that ethanol free anhydrous methylene chloride is used in the solvent.

6. A pharmaceutical composition having mucosecretolytic fluidizing and antibronchospastic activity characterized in that it comprises a mucosecretolytic fluidizing and antibronchospastic active effective amount of the compound of formula (I) of claim 1 and at least one pharmaceutically acceptable vehicle or excipient.

7. A method of treating a respiratory disease characterized in that it comprises administering to a host having a respiratory disease a mucosecretolytic fluidizing and antibronchospastic effective amount of the compound of formula (I) of claim 1.

* * * * *